United States Patent [19]
Czuha, Jr.

[11] 3,954,590
[45] May 4, 1976

[54] IRIDIUM THIN RIBBON ELECTRODES FOR ELECTROCHEMICAL CELLS

[75] Inventor: Michael Czuha, Jr., San Gabriel, Calif.

[73] Assignee: E. I. Du Pont de Nemours and Company, Wilmington, Del.

[22] Filed: Jan. 13, 1975

[21] Appl. No.: 540,451

Related U.S. Application Data

[63] Continuation-in-part of Ser. No. 281,858, Aug. 18, 1972, abandoned.

[52] U.S. Cl............................ 204/195 W; 73/336.5
[51] Int. Cl.²......................................... G01N 27/46
[58] Field of Search........ 73/336.5; 204/1 T, 195 W

[56] References Cited
UNITED STATES PATENTS

| | | | |
|---|---|---|---|
| 1,077,920 | 11/1913 | Stevens | 204/290 F |
| 2,715,667 | 8/1955 | Auwarter | 73/336.5 |
| 2,719,797 | 10/1955 | Rosenblatt et al. | 204/290 F |
| 3,001,918 | 9/1961 | Czuha | 204/195 W |
| 3,168,829 | 2/1965 | Nelson | 73/336.5 |
| 3,223,609 | 12/1965 | Reeds | 204/195 W |
| 3,540,278 | 11/1970 | Diamond et al. | 73/336.5 |
| 3,696,007 | 10/1972 | Bennett | 204/195 W |
| 3,712,860 | 1/1973 | Gabrusenok | 204/195 W |

FOREIGN PATENTS OR APPLICATIONS 941,436  11/1963  United Kingdom............ 204/195 W

*Primary Examiner*—T. Tung

[57] ABSTRACT

Diffusion electrolytic moisture detection cells having either the cathode or both electrodes formed of iridium or an alloy of at least 10 wt.% iridium and a noble metal. The electrodes are from 0.1 to 1 micron in thickness and are supported on either glass or alumina.

7 Claims, 3 Drawing Figures

IRIDIUM THIN RIBBON ELECTRODES FOR ELECTROCHEMICAL CELLS

CROSS-REFERENCE TO RELATED APPLICATION

This application is a continuation-in-part of application Ser. No. 281,858 filed Aug. 18, 1972 by Michael Czuha, Jr., now abandoned.

BACKGROUND OF THE INVENTION

This invention relates to the composition of the electrodes in an electrolytic moisture detection cell of the type employing a normally solid and regenerable hygroscopic electrolyte.

An electrolytic moisture detection cell generally involves two electrodes spaced apart from each other and in contact with a nonconductive substrate. A film of a hygroscopic electrolyte, generally phosporus pentoxide, fills the space between at least a portion of the electrodes. Often, it occupies all of the available space between the electrodes and also coats the electrodes themselves.

Upon the application of an electric potential, the electrolyte, in the absence of any moisture, does not permit current to flow between the electrodes. However, with water present, the electrolyte absorbs moisture; becomes conductive; and electrically bridges the space between adjacent portions of the electrodes.

As the current flows between the electrodes, the water electrolyzes to hydrogen and oxygen. The electrolyte thus continuously regenerates itself. Further, the electrical energy consumed in the electrolysis represents an accurate measure of the moisture absorbed in accordance with Faraday's law.

The composition of the electrodes represents an important consideration in the construction of an electrolytic moisture detection cell. Platinum and palladium wires have found the most frequent use in these electrodes.

J. W. Reeds, Jr., in his U.S. Pat. No. 3,223,609 of Dec. 14, 1965, teaches the use of rhodium or rhodium alloy electrodes wound helically on the inside surface of a cylindrical wall forming part of the cell container. Reeds suggests that using rhodium in these electrodes, or at least the anode, will avoid the development of black metallic deposits between adjacent turns of the two electrodes which previously caused shorting of the cells and ended their useful life. Reeds further recites that, after the electrolysis of water to $H_2$ and $O_2$, the rhodium also reduces the recombination of the hydrolysis products to reform water and give erroneously high results, particularly in gas streams having concentrations of $H_2$ greater than 50%. According to the inventor, alloying the rhodium with any other metal, while producing a cell with a longer life that those totally lacking rhodium, nonetheless engenders inferior cells as compared to those with pure rhodium electrodes, or at least a pure rhodium anode. In particular, Reeds states that iridium represents one metal which, when alloyed with rhodium, produces inferior cell quality than pure rhodium.

Recently, however, electrolytic moisture detection cells have seen the development of a drastically new design for the electrode and electrolyte. This design, discussed below with reference to FIGS. 1, 1A, and 2 utilizes thin ribbon metal electrodes attached to and supported by a nonconductive substrate. This structure generally involves electrodes one micron or thinner. In comparison to the usual helically wound wire electrodes, the thin ribbon electrodes of this design do not possess their own mechanical rigidity. Rather, they must derive their stiffness from the substrate to which they adhere.

Should the thin ribbon electrodes become dislodged and lose contact with the substrate, loss of electrical contact with the hygroscopic electrolyte follows. The electrolytic cell then becomes inactive and useless at those locations where the electrodes have undergone such buckling. As a result, the cell suffers a reduction in its capacity to conduct current and accordingly saturates at abnormally low current levels.

Furthermore, in these inactive cell areas, the hygroscopic electrolyte nonetheless continues to absorb water. However, in order to undergo electrolysis, this moisture must now migrate to active portions of the cell where the electrodes maintain their adherence to the substrate. The period required for this migration represents a deleterious increase in the cell response times.

The problems associated with the loss of contact between the electrode and the substrate increase in severity in electrolytic diffusion cells. In these cells, discussed with regards to FIGS. 1 and 1A below, a diffusion barrier separates the sample undergoing analysis from the electrodes, electrolyte and their immediately adjacent area.

The diffusion cell incurs this increased severity in two regards. First, the diffusion barrier retards the excape of the $H_2$ and $O_2$ hydrolysis products which appears to aggrevate the electrode buckling. Second, the diffusion barrier retards the ingress of moisture from the sample and results in a cell response time already longer than for normal moisture cells; this increased response times necessitated by the diffusion of water from portions of the cell inactivated by buckled electrodes to active cell areas adds to the generally longer diffusion cell response times to give excessively and undesirably long overall response times.

SUMMARY OF THE INVENTION

Including iridium or an alloy thereof with another platinum group metal in the composition of at least one electrode in electrolytic moisture detection cells having thin ribbon electrodes alleviates electrode buckling and its accompanying separation from the substrate. Preferably, both electrodes include one of these metals. However, when only one electrode includes the metal, it should be the cathode. These metals apparently avoid the inclusion of hydrogen within the electrodes in the form of solutions or metal hydrides, which presumably causes the buckling and loss of contact. Preventing such hydrides or hydrogen solutions becomes particularly important in diffusion cells where the hydrogen product of hydrolysis has difficulty in escaping through the diffusion barrier.

The use of iridium or its alloy with a platinum group metal serves to reduce the electrode buckling. Further, iridium alone or when alloyed with platinum appears more amendable to the techniques of metal deposition on the substrate to form electrodes than other metals.

DESCRIPTION OF THE INVENTION

Figure 1:
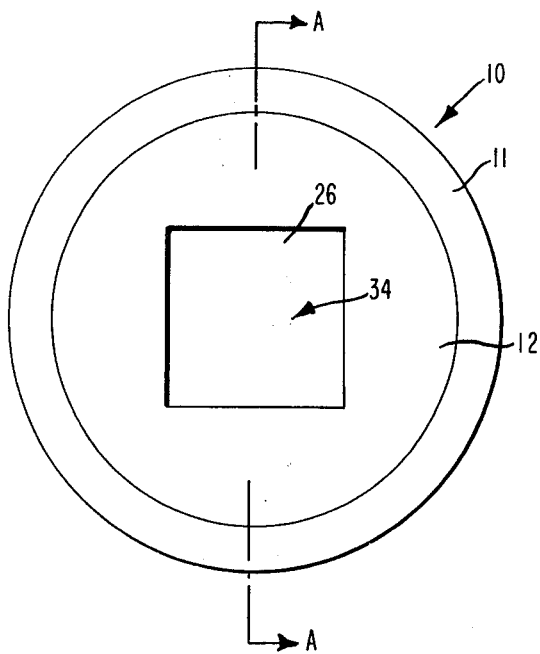
FIG. 1 gives a frontal view of a diffusion electrolytic moisture cell.
Figure 1A:
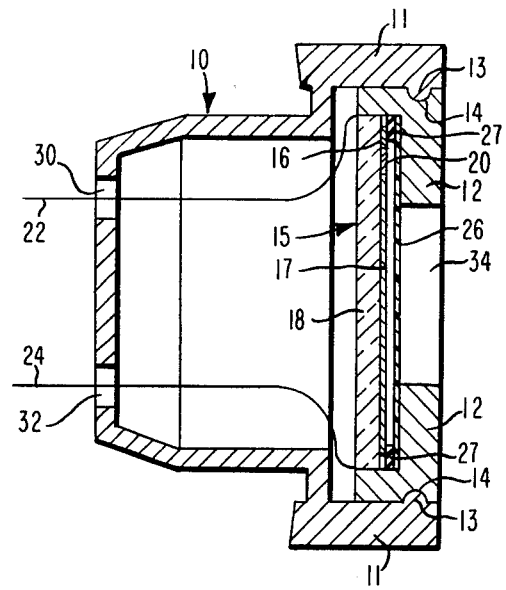
FIG. 1A shows a diffusion cell in a cross sectional view taken along the line A—A of FIG. 1.

Referring to FIGS. 1 and 1A, the diffusion type electrolytic moisture cell along with its uses and advantages received a general description in M. Czuha, Jr.'s U.S. Pat. No. 3,001,918 of Sept. 26, 1961. The cell 10 enclosed by the polyethylene wall 11 and the tetrafluoroethylene ring 12 contains a sensor, indicated generally at 15, which includes a first electrode 16 and a second electrode 17 in contact with the hygroscopic electrolyte substance 20, such as phosphorus pentoxide, on the substrate support 18.

A diffusion barrier 26 along with the spacer ring 27 and the support 18 form an enclosure about the electrodes, 16 and 17, and the hygroscopic layer 20 which preferably is formed of phosphorus pentoxide. The stainless steel ribbon leads 22 and 24 make contact with the electrodes 16 and 17, respectively; pass through openings 30 and 32 in the cell wall 11; and thus, provide electrical connection between these electrodes and the outside. The diffusion barrier 26 may simply have pores extending through it, or alternately can use a thin permeable membrane. A controlled porosity polycarbonate film represents a preferred choice. The retaining ring 12 also provides an opening 34 to allow a sample to contact the diffusion barrier 26.

The sensor 15 forms a tight, press-fit in the retaining ring 12. This not only retains the sensor in place, but also rigidly entraps the membrane 26 and the tetrafluoropolyethylene spacer ring 27. The tight fit of the sensor 15 in the retaining ring 12 also positions the electrical leads 22 and 24 and insures their electrical contact with the electrodes 16 and 17, respectively.

The retaining ring, 12, in turn fits into position in the wall 11. The protruding ring 13 on the wall 11 aligns with the indented ring 14 in the retaining ring 12 and insures a close and tight fit between the two components.

The time required for moisture to diffuse through the barrier 26 increases the response time of the cell to changing moisture conditions. Buckled electrodes necessitating the diffusion of moisture to other areas of the cell would further increase the cell response time. Thus, firmly affixed electrodes find particular use in the diffusion type electrolytic moisture cell.

Figure 2:
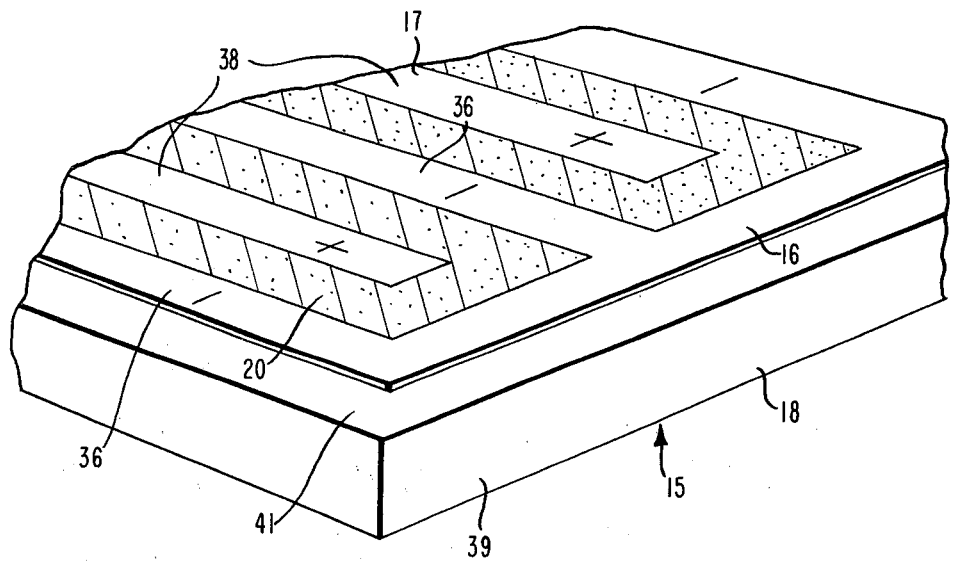
FIG. 2 shows an elevated view of the sensor from FIG. 1A with grid electrodes attached to a substrate.

FIG. 2 shows the sensor 15 in greater detail, looking at a corner of the sensor. The electrodes 16 and 17 contact and adhere to the surface 41 of substrate 18. The hygroscopic substance 20 also adheres to the surface 41 of substrate 18 and fills the spaces between the electrodes 16 and 17. The substrate 18 itself should not conduct appreciable amounts of electricity between the electrodes. Suitable substrates include glass or alumina with the former representing a preferred choice.

The flat thin ribbon electrodes 16 and 17 generally have a thickness in the range of about 0.1 to 1 micron. They generally have a width in the order of approximately 25 microns, and are usually spaced about 12 to 25 microns apart.

The techniques of sputtering or ion beam plating, discussed below, allow the use of a mask during the plating or sputtering in order to achieve a desired electrode pattern on the substrate. The pattern shown in FIG. 2 represents a particularly useful design. Each of the two electrodes 16 and 17 have finger-like extensions 36 and 38, respectively, which intersperse with the extensions of the other electrode. This pattern presents a particularly large area of electrolyte between closely spaced electrodes and, thus, permits rapid electrolysis of any moisture passing through the diffusion barrier 26 of FIGS. 1 and 1A. To aid in visualizing the electrode pattern of FIG. 2, the extensions 36 of the first electrode 16 carry a negative sign, while the extensions 38 of the other electrode 17 bear a positive sign.

Making the electrodes 16 and 17 of metals including iridium or an alloy of at least 10 wt.% iridium with another reduces the buckling of the electrodes on the surface 41 of substrate 18 and the loss of the contact between the electrodes and the substrate. Though any appreciable amounts of iridium in the electrodes produces some beneficial result, incorporating at least about 10% into the above defined electrode alloy composition produces significantly improved behavior over electrodes devoid of these metals. Making the electrodes of pure iridium, or of an alloy thereof with platinum will produce the most desired electrodes. Further, iridium or alloys of at least 10 wt.% iridium and platinum has shown itself more susceptible to firm deposition as a thin metal on the substrate in the first instance.

The usual techniques for depositing thin ribbon electrodes upon the substrate generally produces both electrodes simultaneously. Accordingly, the two electrodes most often have the same composition. However, both electrodes need not have the same composition or, specifically, contain iridium. The hydrogen produced by hydrolysis appears first at the cathode. Accordingly, only this electrode must include the iridium, although, preferably, both have the same composition and both will contain either pure iridium or one of its above defined alloys.

Many techniques have the capability of placing thin ribbons of metal upon substrates. However, techniques not providing a firm bond between electrode and substrate should be avoided. Contrariwise, sputtering and ion beam plating represent methods that do provide for strongly adhering metal electrodes. K. L. Chopra discusses these techniques on pages 24–43 of his book *Thin Film Phenomena* (McGraw-Hill Book Company, New York, 1969). Both of these techniques employ primary ions striking a target of either pure iridium or one of its above defined alloys to produce secondary ions of these metals. The secondary ions possess appreciably higher kinetic energy than thermal ions. Because of this high energy, the secondary ions of iridium, when striking a substrate surface, adhere strongly and accordingly have a high sticking coefficient.

The sputtering technique produces ions possessing a wide spread of energy. Not all possess sufficient energy to ahhere firmly to the surface. Ion beam plating, however, gives generally monoenergetic ions which uniformly adhere to the substrate.

Both of these techniques produce electrodes having uniform thickness. They also allow the development of the narrow electrodes with the close spacing discussed above. A photoresist polymer aids in the development of the actual pattern upon the substrates surface. The preferred method involves the double sputtering technique, often used in integrated circuitry. The double sputtering appears to produce more uniform spacing between the electrodes. The first sputtering step deposits a uniform layer of metal over the entire surface of the substrate. Subsequently, a photoresist polymer covers the previously deposited layer of metal. After exposure through a mask and development, the photoresist covers only those areas of the substrate which are to contain the metal electrodes. In the areas without the polymer, a second sputtering step removes the metal to produce the clear areas on the substrate.

The cell's performance exhibits a dependence upon the nature of the interface between the electrodes and the substrate. A possible problem, in addition to the loss of contact or poor contact between the electrode and the substrate, involves overetching the cell sensor in areas not covered by the electrodes. This results from prolonging the second sputtering step beyond the point required to produce the clear areas on the substrate. This extended sputtering creates an undercut at the electrode edge which a fine pointed scribe can detect. As inferred above, all of these poor interface conditions produce cells which can saturate at low current levels, for example, 5 milliamps, or take inordinately long times to reach their saturation level. Such poor results represent the primary indicators of defective sensors.

What is claimed:

1. An electrolytic moisture detection cell comprising a substrate, spaced apart thin ribbon metal electrodes having a thickness of from about 0.1 to about 1.0 micron attached to and supported by said substrate, said electrodes comprising an anode and a cathode, the cathode being formed of a metal consisting essentially of iridium or an alloy containing at least 10 weight percent iridium and the remainder platinum; and a hygroscopic film deposited on said substrate and filling at least a portion of the space between said anode and said cathode.

2. The electrolytic moisture detection cell of claim 1 wherein said cell is a diffusion electrolytic cell and a diffusion barrier covers the electrodes and the hygroscopic film.

3. The electrolytic moisture detection cell of claim 2 wherein both of said electrodes are formed of said metal.

4. The electrolytic moisture detection cell of claim 3 wherein said metal is substantially pure iridium.

5. The electrolytic moisture detection cell of claim 2 wherein both of said electrodes are attached to and supported by a substrate of glass or alumina.

6. The electrolytic detection cell of claim 5 wherein both of said electrodes are formed of said metal.

7. The electrolytic detection cell of claim 6 wherein said metal is substantially pure iridium.

* * * * *